United States Patent
Bruder et al.

(10) Patent No.: US 8,892,187 B2
(45) Date of Patent: Nov. 18, 2014

(54) METHOD FOR REDUCING STEP ARTIFACTS IN A CARDIO CT REPRESENTATION

(75) Inventors: Herbert Bruder, Höchstadt (DE);
Rainer Raupach, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 1856 days.

(21) Appl. No.: 11/727,751

(22) Filed: Mar. 28, 2007

(65) Prior Publication Data
US 2007/0232888 A1    Oct. 4, 2007

(30) Foreign Application Priority Data
Mar. 29, 2006  (DE) .................. 10 2006 014 625

(51) Int. Cl.
| | |
|---|---|
| *A61B 5/05* | (2006.01) |
| *G06T 3/40* | (2006.01) |
| *A61B 6/00* | (2006.01) |
| *G06T 7/20* | (2006.01) |
| *A61B 6/03* | (2006.01) |

(52) U.S. Cl.
CPC .......... *G06T 3/4007* (2013.01); *G06T 2211/412* (2013.01); *G06T 2207/30048* (2013.01); *A61B 6/5217* (2013.01); *G06T 7/2033* (2013.01); *A61B 6/503* (2013.01); *A61B 6/032* (2013.01)
USPC ........... 600/425; 382/128; 382/131; 382/282; 378/4

(58) Field of Classification Search
USPC .......................... 382/128, 131, 282; 600/407; 375/240.16
See application file for complete search history.

(56) References Cited

U.S. PATENT DOCUMENTS

| | | | |
|---|---|---|---|
| 4,899,393 A | 2/1990 | Morishita et al. | |
| 6,694,047 B1 * | 2/2004 | Farrokhnia et al. | ........... 382/132 |

(Continued)

FOREIGN PATENT DOCUMENTS

| | | |
|---|---|---|
| DE | 103 60 981 A1 | 7/2005 |
| DE | 10360981 A1 | 7/2005 |

(Continued)

OTHER PUBLICATIONS

"Automatic phase point determination for cardiac CT imaging", Robert Manzke et.al. Medical imaging 2004, proc. of SPIE vol. 537, 690-699, 2004.

(Continued)

*Primary Examiner* — Unsu Jung
*Assistant Examiner* — Joseph M Santos Rodriguez
(74) *Attorney, Agent, or Firm* — Harness, Dickey & Pierce, P.L.C.

(57) ABSTRACT

A method is disclosed for reducing step artifacts in the forward increment direction of a cardio CT representation. In at least one embodiment, volume recordings or section images of first and second sub-volumes of a heart volume, which lie adjacent to one another in the forward increment direction and partially overlap in an overlap region, are recorded by a computer tomography system. Each sub-volume's detector data is used for the reconstruction coming from different heart cycles. Finally, a displacement vector relative to a second sub-volume is determined at least for a selected point of the overlap region of a first sub-volume and the second sub-volume is subjected at least partially to a spatial transformation according to the at least one displacement vector.

20 Claims, 4 Drawing Sheets

(56) References Cited

U.S. PATENT DOCUMENTS

| | | | |
|---|---|---|---|
| 6,950,542 B2* | 9/2005 | Roesch et al. | 382/128 |
| 2004/0064036 A1* | 4/2004 | Mao et al. | 600/413 |
| 2005/0063467 A1* | 3/2005 | Hekstra et al. | 375/240.16 |
| 2005/0195937 A1 | 9/2005 | Bruder et al. | |
| 2006/0002631 A1* | 1/2006 | Fu et al. | 382/294 |

FOREIGN PATENT DOCUMENTS

| | | |
|---|---|---|
| EP | 1394747 | 3/2004 |
| JP | 62186381 A | 8/1987 |
| JP | 62189582 A | 8/1987 |
| JP | 5130984 A | 5/1993 |
| JP | 10137231 A | 5/1998 |
| JP | 2004081866 A | 3/2004 |
| JP | 2004147084 A | 5/2004 |
| JP | 2005270635 A | 10/2005 |
| WO | WO 2006082192 A1 * | 8/2006 |

OTHER PUBLICATIONS

Manzke, R. et al., "Automatic phase determination for retrospectively gated cardiac CT," Med. Phys. 31 (12), pp. 3345-3362, Dec. 2004.

* cited by examiner

METHOD FOR REDUCING STEP ARTIFACTS IN A CARDIO CT REPRESENTATION

PRIORITY STATEMENT

The present application hereby claims priority under 35 U.S.C. §119 on German patent application number DE 10 2006 014 625.5 filed Mar. 29, 2006, the entire contents of which is hereby incorporated herein by reference.

FIELD

Embodiments of the invention generally relate to a method for reducing step artifacts of a cardio CT representation. For example, they may relate to one wherein volume recordings or section images of two sub-volumes of a heart volume, which lie adjacent to one another in the forward increment direction and partially overlap in an overlap region, are recorded by a computer tomography system (CT), and each sub-volume's detector data used for the reconstruction are taken from different heart cycles.

BACKGROUND

It is known that when cardio CT recordings of the heart are being taken, step artifacts can occur because the heart's volume represented overall is composed of a plurality of sub-volumes whose reconstruction data are respectively recorded in different heart cycles. The previous method for reducing such step articles consists in block-specific selection of the reconstruction phase. This may be done both manually and automatically by searching for the time with the least motion. This method is known by the name "Motion Mapping" and is described in detail in the publication "Automatic phase determination for retrospectively gated cardiac CT", Manzke, R. et al., Med. Phys. 31 (12), pp 3345-3362, December 2004. In some cases, this method delivers a better result than a constant reconstruction phase throughout the entire data set.

It has been found, however, that this method does not eliminate all step artifacts which occur in cardio CT recordings.

SUMMARY

In at least one embodiment of the invention, an improved method is disclosed for reducing the step artifacts in cardio CT recordings, which also reduces or even eliminates the step artifacts which are not due to motion during the data acquisition.

The inventors have discovered that another reason for the occurrence of step artifacts in cardio CT recordings is that the heart may experience a spatial offset between the resting phases, the data from which are used to reconstruct the CT recordings. Although the heart is not in motion in the resting phases of the successive heart cycles, neither is it necessarily at the same position. This may involve a displacement of the entire heart or merely a displacement of the heart region currently being scanned. If differing positions in successive heart phases are the cause of the step artifact, then even an optimized phase relation cannot provide an improvement of the imaging. When assembling the reconstructed sub-volumes, it is thus necessary to join them together so as to take the heart contour into account rather than the relative orientation with respect to the CT.

Only particular temporal data windows are used in a spiral CT of the heart, which generally lie in the region of the diastolic plateau. With a sufficiently fast rotation of the gantry, this makes it possible to reconstruct virtually motion-free and therefore artifact-free images. In one heart phase, however, it is at most possible to record a volume corresponding to the width of the detector in the forward increment or z direction, so that the overall volume must be assembled from blocks recorded in different heart cycles, so-called "stacks". In this case, either the individual stacks may consist of a multiplicity of reconstructed section images or they may represent voxel-wise reconstructed sub-volumes.

The motion curves of the various regions of the heart are not necessarily the same in each cycle. Therefore although each stack may be consistent per se, i.e. artifact-free, an offset may nevertheless occur between different blocks owing to different positions of the resting plateau.

This effect is perceptible and perturbing for the diagnosis particularly when the displacement takes place in the x/y plane. A global mutual displacement of the stacks does not necessarily resolve this problem since the offset may be locally different, i.e. for example the LCA (=left coronary artery) may exhibit a different position change than the chamber wall. Although the time resolution can be systematically optimized in order to reduce motion artifacts by increasing the gantry rotation speed or using multi-tube CT systems, the described problem is physiological in nature and cannot thereby be remedied.

When assembling sequentially recorded sub-volumes to form an overall image of the heart, it is thus necessary to carry out spatial transformations of the sub-volumes taking into account the offset of the heart between the individual resting phases or recording phases. In this context, it should also be noted in particular that merely a linear transformation of the entire sub-volume is usually not sufficient; rather it may be necessary to construct a vector field which generates a position-dependent spatial transformation similarly to a morphing method, which is aimed at significant contours in overlap regions of reconstructed sub-volumes.

In at least one embodiment, the inventors therefore propose an improvement of a method for reducing step artifacts in a cardio CT representation, in which volume recordings or section images of two sub-volumes of a heart volume, which lie adjacent to one another in the forward increment direction and partially overlap in an overlap region, referred to hereafter as the first and second sub-volumes, are recorded by a computer tomography system (CT), each sub-volume's detector data used for the reconstruction coming from different heart cycles. The improvement resides in determining a displacement vector relative to a second sub-volume at least for a selected point of the overlap region of a first sub-volume, and in subjecting the second sub-volume at least partially to a spatial transformation according to the at least one displacement vector.

In at least one embodiment of this method, the at least one displacement vector may be determined perpendicularly to the forward increment direction or in three-dimensional space. The former variant compensates merely for step artifacts in an image plane perpendicular to the system axis, while the second variant can also eliminate spatially oriented displacements and step artifacts resulting therefrom.

It is furthermore favorable to determine a field of displacement vectors over the entire overlap region, instead of a single displacement vector. This primarily accommodates the situation in which the displacement does not take place uniformly at all points, but may be position-dependent.

The identification and definition of displacements is furthermore particularly simplified by determining the at least one displacement vector between significantly pronounced image points. In particular, a high contrast change and its vicinity may be used as significantly pronounced image points.

It is furthermore advantageous, in order to determine the at least one displacement vector, that the overlap regions of the first and second sub-volumes should be displaced relative to one another in the vicinity of significant points until a minimal error is achieved in the comparison of both overlap regions, and that this displacement used therefor should be used as an optimal displacement vector.

If a field of displacement vectors is determined instead of a single displacement vector or a few displacement vectors, then it is advantageous when determining a field of displacement vectors to compare individual significant points of the overlap region, to determine their optimal displacement vector and to determine displacement vectors lying in-between by interpolation calculation.

According to a simple variant of the method according to at least one embodiment of the invention, the second sub-volume may be fully transformed in order to match the second sub-volume to the first sub-volume. Furthermore, the second sub-volume may be transformed equally over the entire sub-volume in order to match the second sub-volume to the first sub-volume.

It is however particularly advantageous for the second sub-volume to be transformed with a vector field, whose displacement vectors are aligned differently and are of different size, in order to match the second sub-volume to the first sub-volume. In this case, for example, its displacement vectors may be shortened, preferably constantly and/or toward zero, with an increasing distance from the overlap region.

BRIEF DESCRIPTION OF THE DRAWINGS

The invention will be explained in more detail below with reference to an example embodiment with the aid of the figures, wherein only the features necessary for understanding the embodiments of invention are represented. Here, the following references are used: 1: CT system; 2: first X-ray tube; 3: first detector; 4: second X-ray tube; 5: second detector; 6: gantry housing; 7: patient; 8: patient support; 9: forward increment direction/system axis; 10: control and computation unit; 11: memory; 13: significantly pronounced image point in the overlap region; 14: displacement vector; 15: overlap region; I, I': section images; N,N−1,N+1: sub-volumes; P: position; $S_x$: selection mask; t: time; z: forward increment direction/system axis; $\Delta t$: time window; $\Delta P$: offset.

In detail.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the term "and/or" includes any and all combinations of one or more of the associated listed items.

Figure 1:
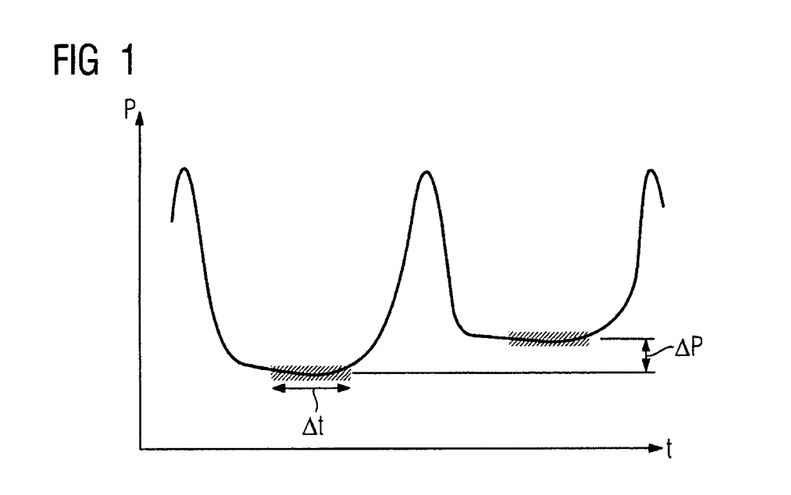
FIG. 1 shows schematic motion curves of a heart.

FIG. 1 schematically shows the actual problem on which an embodiment of the invention is based with the aid of the position variation of the heart, i.e. by motion curves over two heart cycles. The profile of the position P at an arbitrary point of the heart is plotted against time t. In both cycles, a region which corresponds to the resting phase of the heart in the diastole is respectively shaded. In this region with the time window $\Delta t$, one sub-volume of the heart is scanned and reconstructed per heart cycle. Ideally, it is assumed in the prior art that the heart and every point of the heart lies at the same position in each cycle phase. As can be seen from FIG. 1, however, the positions of the relevant point of the heart differ by an offset $\Delta P$. In practice, in order to represent the heart, a plurality of sub-volumes which come from different heart cycles are assembled to form an overall image of the heart.

Figure 2:
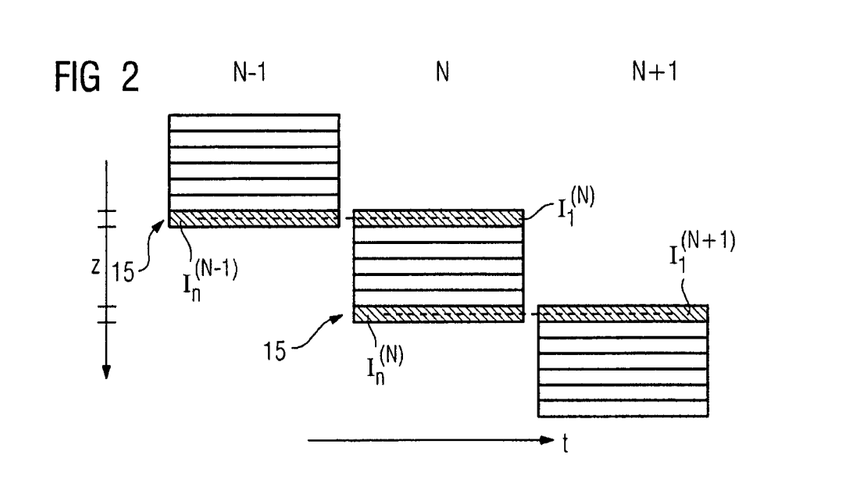
FIG. 2 shows a schematic representation of three reconstructed stacks with overlap regions plotted against the forward increment direction z and time.

This is shown by way of example in FIG. 2 with the aid of a plurality of so-called stacks (=stacks of section images from a heart phase). The individual stacks N−1, N and N+1, which respectively consist of 1, . . . ,n section image planes $I_n^{(N-1)}$, $I_n^{(N)}$ and $I_n^{(N+1)}$, are shown against the time axis t, the first and last section image represented by shading respectively overlapping with the last and first section image of the neighboring stack (=Overlap region 15).

If these stacks are simply lined up in space as is previously the case, then a congruent transition is not obtained and the representation includes step artifacts. The method according to an embodiment of the invention is provided for reducing step artifacts at the stack boundaries as presented above, an example embodiment being explicitly described below on the basis of section image reconstructions.

Step 1:

A reconstruction of image data is carried out in the first step, a so-called cardio reconstruction with temporal selection of data segments, which comprises the property that there is respectively at least one section image with an identical z position at the block boundaries. Since the table forward increment in the z direction per unit time is in any case usually selected with an appropriate safeguard against the variation in the heart rate during the scan, since gaps would occur in the image stack with too fast a driving rate and thin layers may be reconstructed without restriction, this is generally possible automatically and therefore requires no modification of the usual scan parameters.

Without restriction of generality, it will be assumed below that all stacks contain the same number n of images.

Step 2:

An analysis of the offset between neighboring stacks is now carried out in the second step. This analysis of motion between neighboring stacks need not necessarily take place in the entire image plane, rather it may expediently be carried out only at the points where high contrast changes occur, for example soft tissue <-> contrasted vessel, lung tissue <-> soft tissue. In homogeneous regions, on the one hand, the displacements cannot be detected accurately, and on the other hand the eye will scarcely perceive a possible offset. Furthermore, restricting the pixels taken into account has a positive effect in relation to the required computation time.

The relevant regions may, for example, be selected by thresholding on the basis of pixel values or gradients. For each pixel p of the last layer of each stack, linear variances $v_p^i$ may particularly advantageously be calculated in numerous directions i=1, . . . ,m, e.g. m=4. For a fixed pixel p let $i_{min}(p)$ (or $i_{max}(p)$) be the index with minimal or maximal variance. Then, $$\overline{V}_{min} = \frac{\sum_p v_p^{i_{min}(p)}}{\sum_p 1} \quad (1)$$

defines a quantity which is characteristic of the noise of the image in question, but is free of structural noise. For each pixel, a contrast-to-noise ratio $$CNR(p) = \frac{v_p^{i_{max}(p)}}{\overline{V}_{min}} \quad (2)$$

can be calculated therefrom. A suitable selection is given by the criterion CNR(p)>T, from which a corresponding mask S is obtained.

Figure 3:
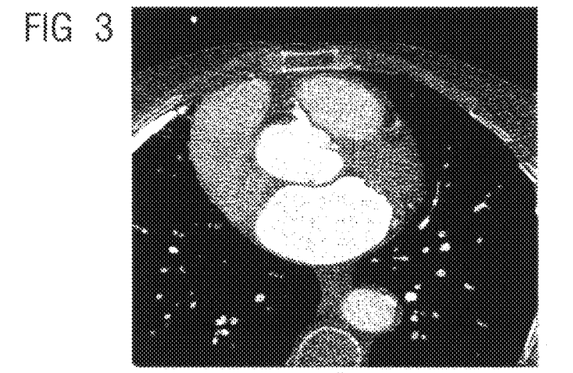
FIG. 3 shows a CT section image of a heart.
Figure 4:
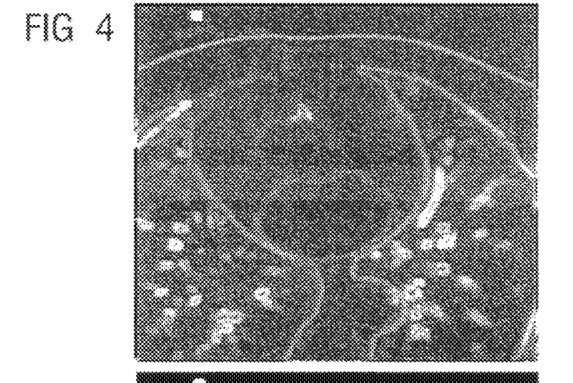
FIG. 4 shows a CNR(p) according to formula (2)
Figure 5:
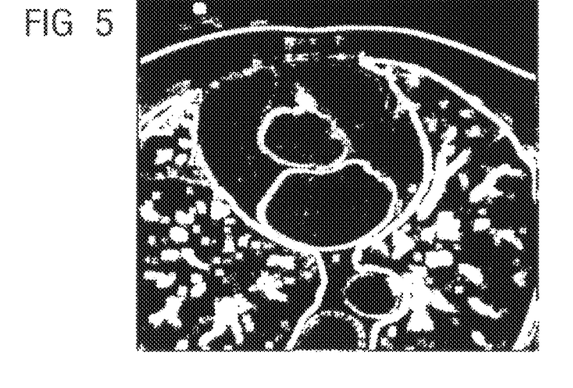
FIG. 5 shows a selection mask S based on threshold value operation from CNR(p)

FIGS. 3 to 5 represent this procedure pictorially. FIG. 3 shows an example embodiment of CT image, to which Formula (2) is applied and which leads to the image in FIG. 4. A threshold value operation on the image in FIG. 4 yields the selection mask S, which is shown in FIG. 5.

Step 3:

In the third step, a displacement vector is determined for each pixel p masked in the second step from among the set S. To this end, with reference to the example of the interface $I_n^{(N)}/I_1^{(N+1)}$ at the pixel p in $I_n^{(N)}$, a search is made for that pixel $p'_{opt}(p)$ in $I_1^{(N+1)}$ in whose vicinity U the image content in $I_1^{(N+1)}$ corresponds best to that in $I_n^{(N)}$ around p. The quantities p and p' in this case represent vectors which contain the coordinates of the corresponding pixel. In practice, this may for example be done by minimizing the error integral $$\varepsilon(p') = \sum_{\Delta p \in U} (I_n^{(N)}(p + \Delta p) - I_1^{(N+1)}(p' + \Delta p))^2 \quad (3)$$

by variation of p'. $\Delta p$ is in this case to be understood as a relative vector which extends over all points in the selected vicinity U. The search range of p' is advantageously restricted to a certain range B(p), which is defined by the maximum expected displacement. As a result, $$M^{(N)}(p) = p'_{opt}(p) - p \quad (4)$$

represents the desired displacement field for all p in S, with which $I_n^{(N)}$, restricted to S, must be transformed in order to merge step-free into $I_1^{(N+1)}$. The procedure described here is also known as "block matching".

In the same context a confidence parameter may be calculated for future use, which indicates how reliable the values determined in (4) are. This property is for instance characterized by how "sharp" the minimum of $\varepsilon(p')$ is. In a homogeneous zone, $\varepsilon(p')$ would be virtually constant; in the event of a straight edge, the function scarcely changes when p' is displaced along the edge. In these cases, $p'_{opt}(p)$ or M(p) is not therefore reliable. A measure of the quality of the minimum would for example be $$Q(p) = 1 - \frac{\sum_{p' \in B(p)} \begin{cases} 1 & \varepsilon(p') - \varepsilon(p'_{opt}(p)) < \Delta\varepsilon \\ 0 & \text{otherwise} \end{cases}}{\sum_{p' \in B(p)} 1}, \quad (5)$$

i.e. an analysis of the number of points of $\varepsilon(p')$ inside an interval $\Delta\varepsilon$ around the minimum. It may furthermore be expedient to take the absolute value of $\varepsilon(p'_{opt}(p))$ into account, in order to pick up the situation in which an object is visible in $I_1^{(N+1)}$ owing to a displacement in the z direction, but is not visible in $I_n^{(N)}$.

Less reliable values in M(p) may, depending on Q(p), be replaced by vectors interpolated from neighboring vectors, or mixed with interpolated vectors as a function of Q(p).

The result field may optionally then be smoothed linearly or nonlinearly, in order to eliminate anomalies and thus accommodate the assumption that the displacement field does not change arbitrarily rapidly.

Step 3 may alternatively be addressed by interchanging $I_n^{(N)}$ and $I_1^{(N+1)}$, in order to generate a field $\hat{M}^{(N)}(p')$ for p' in S', which describes the distortion of $I_1^{(N+1)}$ necessary in order to merge step-free into $I_n^{(N)}$. $\hat{M}$ is therefore the inverse function of M and is defined on the set S', which is calculated on $I_1^{(N+1)}$ according to step 2.

Step 4:

So far only the displacement vectors in S have been determined. So that the images of the adjacent stack can be transformed, it is first necessary to fill the "gaps" i.e. the image points outside S. This means that the field M must be extended constantly over the entire image $I_n^{(N)}$, for example by successive propagation taking the already existing neighboring vectors into account. Constantly, in this case, refers to the remark in step 3 that the displacement vectors may be assumed to change only at a limited rate. The propagation of the displacement vectors is advantageously carried out so that the divergence of the vector field outside S is kept as small as possible, and in the ideal case is zero, i.e. it includes as few sources as possible. Methods suitable for this are known from mathematics (Neumann boundary condition) and their application in electrodynamics.

Finally, the displacement field must be propagated over the entire stack N. Let $\Phi_1^{(N)}, \ldots, \Phi_n^{(N)}$ be the fields used for the transformation in the subsequent step 5 for the images $I_1^{(N)}, \ldots, I_n^{(N)}$. Various methods are possible here, three of which will be mentioned below.

a) All images inside a stack are distorted identically, i.e. $\Phi_1^{(N)} = \Phi_2^{(N)} = \ldots = \Phi_n^{(N)}$. In this case the first stack remains unchanged $\Phi_i^{(1)} \equiv 0$, and the $N^{th}$ stack must be transformed by $$\Phi_i^{(N)} \equiv \sum_{k=1}^{N-1} \hat{M}^{(k)}.$$

b) One end of the stack i.e. image $I_1^{(N)}$ or $I_n^{(N)}$ remains unaffected, i.e. $\Phi_1^{(N)} \equiv 0$ or $\Phi_n^{(N)} \equiv 0$. The other end is respectively distorted so that distortion-free connection is possible, i.e. $\Phi_n^{(N)} = M^{(N)}$ or $\Phi_1^{(N)} = \hat{M}^{(N-1)}$. In between, the displacement fields are generated by a continuous transition, i.e. in a linear fashion with $$\Phi_i^{(N)} = \frac{i-1}{n-1} M^{(N)}$$

or $$\Phi_i^{(N)} = \left(1 - \frac{i-1}{n-1}\right) \hat{M}^{(N-1)}.$$

c) The middle of the stack is fixed and a symmetrical distortion takes place at the edges, i.e. $\Phi_1^{(N)} = \hat{M}^{(N-1)}/2$ and $\Phi_n^{(N)} = M^{(N)}/2$. All other displacement vectors are generated by a continuous transition, for example in a linear fashion with $$\Phi_i^{(N)} = \begin{cases} \left(\frac{1}{2} - \frac{i-1}{n-1}\right) \hat{M}^{(N)} & i \leq \frac{n+1}{2} \\ \left(\frac{i-1}{n-1} + \frac{1}{2}\right) M^{(N)} & i > \frac{n+1}{2} \end{cases} \quad (6)$$

Step 5:

As a result of step 4, displacement vectors are available for all images of the stack, and these are now used in order to distort the image contents in this block with the aid of a non-rigid transformation. According to design, the step artifacts at the interface between the stacks N and N+1 are reduced.

Figure 6:
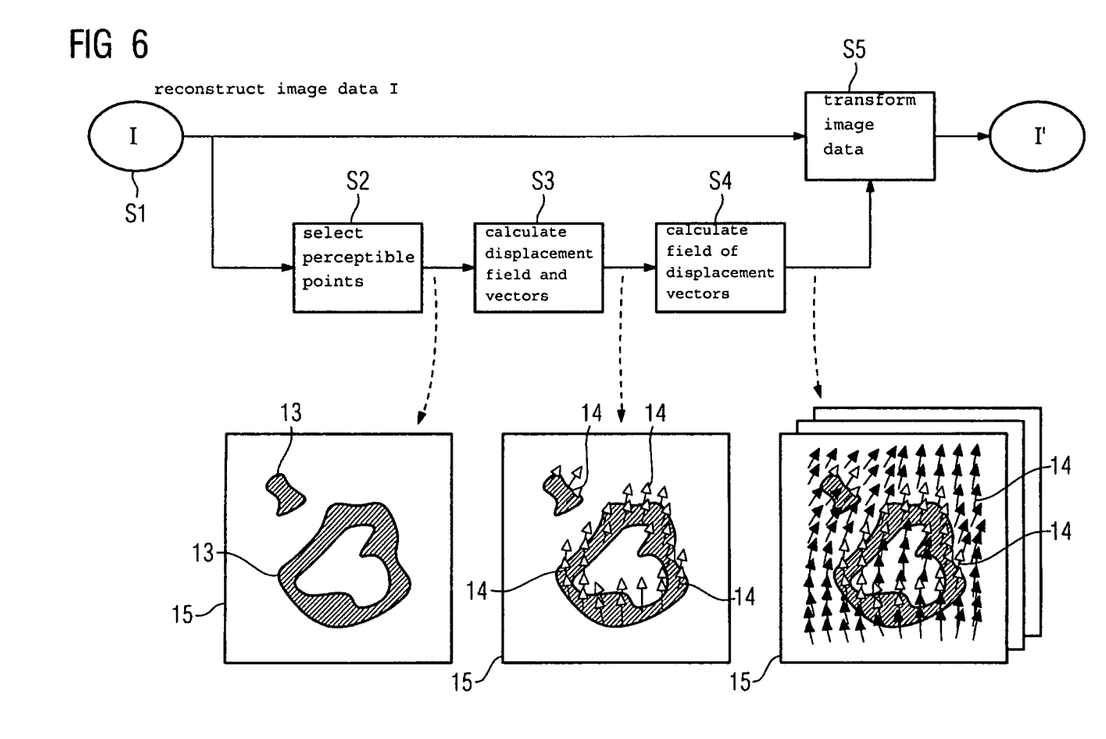
FIG. 6 shows a method according to an embodiment of the invention in a flow chart with a schematic representation of a field of displacement vectors.

FIG. 6 once more represents an embodiment of the method as described above schematically and compactly. The image data I is reconstructed in the first step S1. In the second step S2, the significantly perceptible points of the overlap region 15 are selected with a spatial offset. The displacement field with its displacement vectors 14 is subsequently calculated in the third step S3, in which case a confidence assessment and smoothing may also be carried out. The entire field of the displacement vectors 14 is subsequently calculated in the fourth step S4, so that no new discontinuities and artifacts are created. Lastly, in the fifth step S5, a non-rigid plane or optionally spatial transformation of the image data of one stack to the adjacent stack is carried out, so as to create an artifact-free representation I' of the entire volume of the heart.

It is expressly pointed out that the method according to an embodiment of the invention as presented above may be applied not only to section image representations but also to volume representations, without departing from the scope of the invention. In particular, instead of the offset of structures described only two-dimensionally for clearer understanding, the method may also take into account a spatial offset of heart structures and resolve volume artifacts resulting therefrom.

Figure 7:
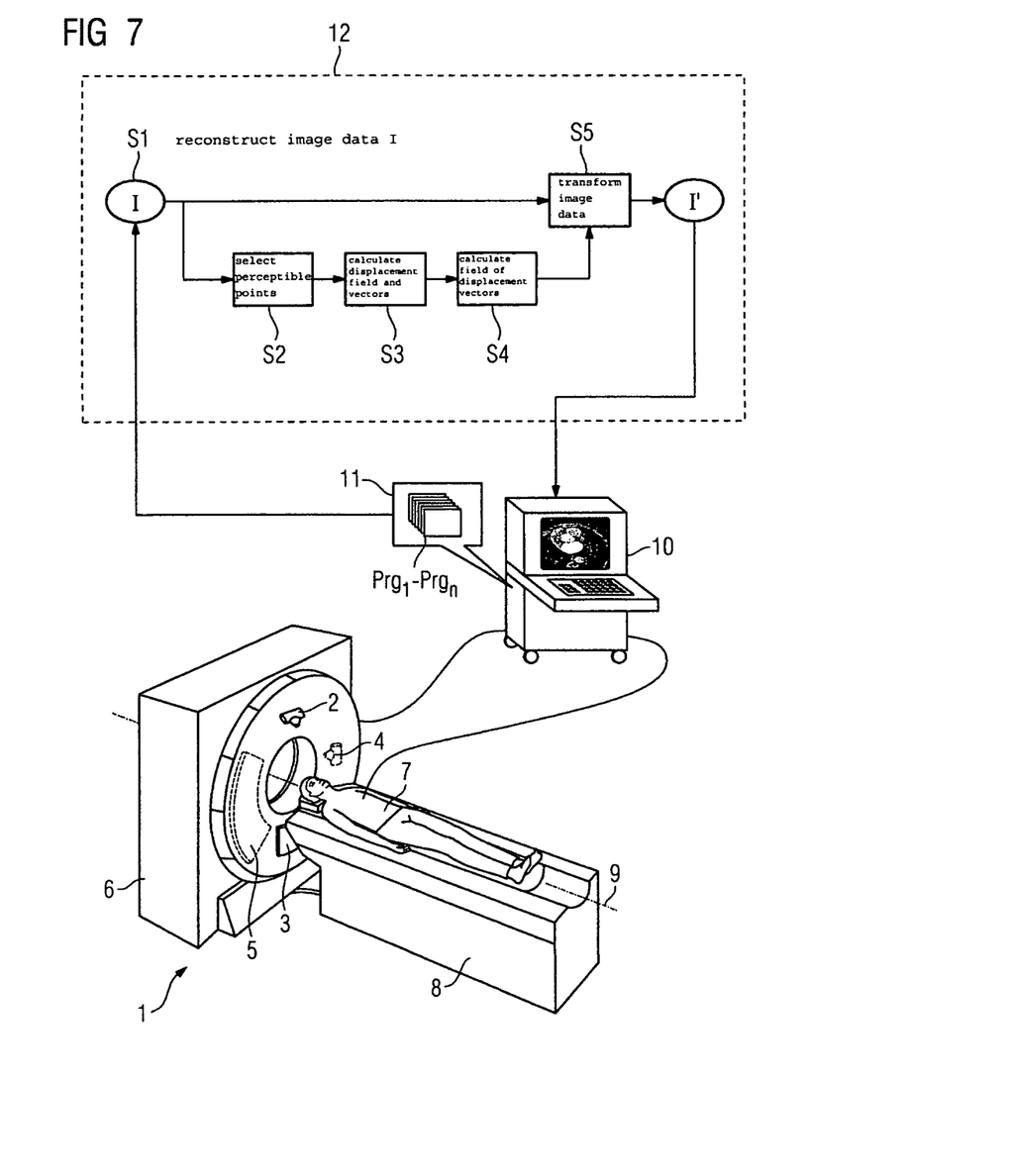
FIG. 7 shows a diagrammatic representation of a CT system with a computation unit and programs for carrying out the method according to an embodiment of the invention.

By way of example, FIG. 7 also shows a CT system 1 whose computation unit 10 contains a storage medium onto which programs are stored for controlling the CT system and evaluating detector output data, including for carrying out the method according to an embodiment of the invention as described above.

The CT system 1 in the case specifically represented here includes a gantry housing 6 in which an X-ray tube 2 and a multiline detector 3 are fastened on the gantry (not represented). During operation, the X-ray tube 2 and the detector 3 are rotated about the system axis 9, while the patient 7 is displaced along the system axis 9 with the aid of the drivable patient support 8 through the scan region between the X-ray tube 2 and the detector 3. A spiral scan is thus carried out relative to the patient. Optionally, a plurality of tube/detector combinations may also be used for the scan. Such a second tube/detector combination is indicated in dashes by the second X-ray tube 4 shown and the second multiline detector 5. The use of a second tube/detector combination improves the time resolution of the cardio recordings. In the example represented here, the control and computation unit 10 also fulfils the function of an ECG with which the heart lead signals, which are usually necessary for correctly phased reconstruction, are determined.

The CT system and the image reconstruction, including image processing, are controlled by the computation unit 10 which, on an internal memory 11, contains computer programs $Prg_1$ to $Prg_n$ that may also be transferred on mobile storage media. Besides the otherwise customary tasks of a CT computer, these computer programs also carry out the image processing method according to an embodiment of the invention.

The schematic representation of FIG. 7 shows a variant of an embodiment of the inventive artifact suppression in the dashed box 12. According thereto, section images or volume data sets I of the patient 7 are first reconstructed with the aid of computer programs $Prg_x$. By the method steps S1 to S5 described above in FIG. 6, the step artifacts are reduced and as a result an improved representation of the section image or volume data sets I' is output on the display of the computer unit 10.

It is to be understood that the features of the embodiments of the invention as mentioned above may be used not only in the combination respectively indicated, but also in other combinations or in isolation, without departing from the scope of the present invention.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reducing step artifacts in a forward increment direction of a cardio CT representation, the method comprising:
    recording at least one of (1) volume recordings of first and second sub-volumes of a heart volume and (2) section images of the first and second sub-volumes of the heart volume, which lie adjacent to one another in the forward increment direction and partially overlap in an overlap region, by a computer tomography system, detector data of each sub-volume being used for a reconstruction coming from different heart cycles;
    determining contrast-to-noise ratios for pixels in the first sub-volume, respectively;
    selecting first points of the overlap region of the first sub-volume based on the contrast-to-noise ratios associated with the pixels in the first sub-volume, pixels having a contrast-to-noise ratio exceeding a threshold being in the overlap region;
    selecting second points of the overlap region of the second sub-volume, wherein each second point is selected according to a correspondence between image contents in the vicinity of a corresponding first point and the second point, respectively;
    determining a field of displacement vectors relative to the second sub-volume based on differences between the first selected points in the overlap region of the first sub-volume and the corresponding second selected points of the overlap region of the second sub-volume, the differences representing displacements between the first selected points and the corresponding second selected points; and
    subjecting at least a region of the second sub-volume that does not overlap the first sub-volume to a spatial transformation according to the field of displacement vectors, thereby reducing the step artifacts.

2. The method as claimed in claim 1, wherein the field of displacement vectors are determined perpendicularly to the forward increment direction.

3. The method as claimed in claim 2, wherein the field of displacement vectors are determined in three-dimensional space.

4. The method as claimed in claim 1, wherein the field of displacement vectors are determined in three-dimensional space.

5. The method as claimed in claim 1, wherein the field of displacement vectors are determined over an entire overlap region.

6. The method as claimed in claim 5, wherein, when determining the field of displacement vectors, individual points of the overlap region are compared, an optimal displacement vector is determined and displacement vectors lying in between are determined by at least one of interpolation and extrapolation calculation.

7. The method as claimed in claim 1, wherein the differences include high contrast changes.

8. The method as claimed in claim 1, wherein, the field of displacement vectors are determined such that a minimal error is achieved the first and second sub-volumes are displaced relative to one another using the field of displacement vectors.

9. The method as claimed in claim 1, wherein, when subjecting the second sub-volume to the spatial transformation, the second sub-volume is fully transformed.

10. The method as claimed in claim 1, wherein, when subjecting the second sub-volume to the spatial transformation, the second sub-volume is transformed equally over an entire sub-volume.

11. The method as claimed in claim 1, wherein, when subjecting the second sub-volume to the spatial transformation, the second sub-volume is transformed with the field of displacement vectors, each of the field of displacement vectors being aligned differently and being of different magnitude.

12. The method as claimed in claim 11, wherein the magnitudes of each of the field of displacement vectors is decreased with an increasing distance from the overlap region.

13. The method as claimed in claim 12, wherein the field of displacement vectors are shortened at least one of constantly and toward zero.

14. A non-transitory storage medium, at least one of integrated in a computation unit and for a computation unit of a CT system, including at least one computer program or program module that, when executed, causes the computation unit of the CT system to carry out the method as claimed in claim 1.

15. A non-transitory computer readable medium including at least one computer program or program module for, when executed on a computer device of a CT system, causing the computer device of the CT system to implement the method of claim 1.

16. The method of claim 1 wherein the first and second sub-volumes at most partially overlap.

17. An apparatus for reducing step artifacts in a forward increment direction of a cardio computer tomography (CT) representation, the apparatus comprising:
    a CT system configured to,
    record at least one of (1) volume recordings of first and second sub-volumes of a heart volume and (2) section images of the first and second sub-volumes of the heart volume, which lie adjacent to one another in the forward increment direction and partially overlap in an overlap region, detector data of each sub-volume being used for a reconstruction coming from different heart cycles;
    determine contrast-to-noise ratios for pixels in the first sub-volume, respectively
    select first points of the overlap region of the first sub-volume based on the contrast-to-noise ratios associated with the pixels in the first sub-volume, pixels having a contrast-to-noise ratio exceeding a threshold being in the overlap region;
    select second points of the overlap region of the second sub-volume, wherein each second point is selected according to a correspondence between image contents in the vicinity of a corresponding first point and the second point, respectively;

determine a field of displacement vectors relative to the second sub-volume based on differences between the first selected points in the overlap region of the first sub-volume and the corresponding second selected points of the overlap region of the second sub-volume, the differences representing displacements between the first selected points and the corresponding second selected points; and subject at least a region of the second sub-volume that does not overlap the first sub-volume to the at least one displacement vector, to reduce the step artifacts.

18. The apparatus as claimed in claim 17, wherein the field of displacement vectors are determined perpendicularly to the forward increment direction.

19. The apparatus as claimed in claim 17, wherein the field of displacement vectors are determined in three-dimensional space.

20. The apparatus as claimed in claim 17, wherein the field of displacement vectors are determined over an entire overlap region.

* * * * *